United States Patent [19]

Shen

[11] Patent Number: 4,901,211
[45] Date of Patent: Feb. 13, 1990

[54] HAT STRUCTURE FOR DISPLAYING INDICIA ILLUMINATED BY A LIGHT

[76] Inventor: Wayne Shen, 7FL-5, No. 1031, Min Shen E. Rd., Taipei, Taiwan

[21] Appl. No.: 281,657

[22] Filed: Dec. 9, 1988

[51] Int. Cl.⁴ .............................................. F21L 15/14
[52] U.S. Cl. ................................... 362/106; 362/105; 2/12; 2/199
[58] Field of Search ............... 362/103, 105, 106, 812; 40/329; 2/12, 199, 185 R, 209.2, 422

[56] References Cited

U.S. PATENT DOCUMENTS

| | | | |
|---|---|---|---|
| 1,493,463 | 5/1924 | Brock | 2/199 X |
| 1,572,210 | 2/1926 | Kolibai | 362/106 |
| 1,744,777 | 1/1930 | Lundgren | 362/106 |
| 2,203,028 | 6/1940 | Parrello | 362/106 |
| 4,667,274 | 5/1987 | Daniel | 362/106 |

Primary Examiner—Ira S. Lazarus
Assistant Examiner—Peggy Neils
Attorney, Agent, or Firm—Morton J. Rosenberg; David I. Klein

[57] ABSTRACT

A hat structure is provided for displaying indicia illuminated by a light mounted to the hat structure. Indicia in the form of text or advertising figures may be displayed by an illuminating light and the hat structure may be unitarily formed in molded construction. A groove (11) is formed within a portion of a visor (1) with the groove (11) being used for insert of a board member (2). Fence walls (12) are provided on a lower surface of the visor (1) with an arcuate board cover member (3) being insertable within the groove (11) for constraining indicia bearing board member (2). The arcuate board cover member (3) includes a boss plate (33) to which is rotatably mounted a switch body (4) having a housing containing a power board (43) electrically coupled to printed circuitboard member (2) for controlling illumination of the indicia, text or advertisements.

3 Claims, 6 Drawing Sheets

FIG. IA
FIG. IB

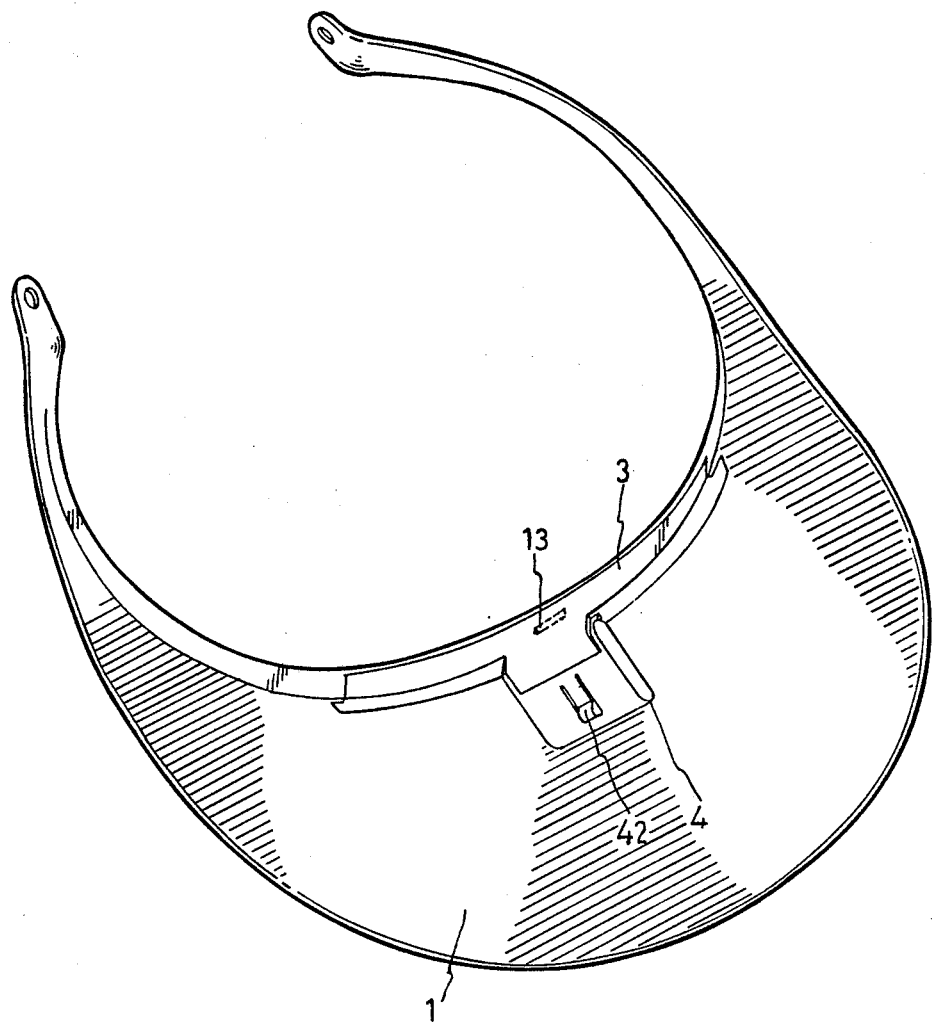
FIG. IC

HAT STRUCTURE FOR DISPLAYING INDICIA ILLUMINATED BY A LIGHT

BACKGROUND OF THE INVENTION

1. Field of the Invention

This invention pertains to a that structure for displaying indicia illuminated by a light mounted on the hat structure. In particular, this invention directs itself to a unitarily formed visor having means for insertion of a board member having indicia formed thereon and illuminated by a light mounted on the board member. Still further, this invention pertains to a hat structure for displaying indicia illuminated by a light mounted to the hat structure wherein a visor includes an arcuate groove for insert of the indicia bearing board member. Additionally, an arcuate board cover member is insertable within the arcuate groove formed in the visor and includes a boss plate which is rotationally coupled to a switch body housing. More particularly, this invention relates to a hat structure for displaying indicia wherein a switch body housing includes a recess chamber for insert of a power board having a battery mounted thereon. More particularly, this invention directs itself to a hat structure for displaying indicia illuminated by a light which includes a switch body housing encompassing a power board wherein both the power board and the switch body are rotationally coupled to an arcuate board cover which in itself is mounted to the visor. Still further, this invention directs itself to a switch body housing which is rotationally coupled to an arcuate board cover member to allow access to a power board by rotational actuation of the switch body housing with respect to the arcuate board cover.

1. Prior Art

Hats having visors are well-known in the art. In general, hats are worn in sunny areas and are limited to protection of the user's face from the sun. Prior art hat structures are relegated to protection of the user's face and do not provide differing exterior designs to attract consumers, or for advertisement purposes.

Such prior art hat structures do not provide for designs which show indicia and advertising figures illuminated by a light, as is necessary to the inventive concept of the subject invention. Additionally, such prior art hat structures do not provide for an alarm function as may be accomplished with the subject matter of the instant concept.

SUMMARY OF THE INVENTION

A hat structure is provided for displaying indicia illuminated by a light mounted to the structure. The hat structure includes a unitarily formed visor defining a lower surface having a pair of fence wall members extending therefrom. The visor has an arcuate groove formed therein. Additionally, the visor has a pair of assist board members formed on opposing ends of the arcuate groove and a rib member formed substantially central of the arcuate groove extension. A board member is provided having indicia formed thereon and is illuminated by a light mounted on the board member. An arcuate board cover member contiguously interfaces with the arcuate groove and is insertable therein. The arcuate board member has a centrally located opening for insert of the rib member therein. The arcuate board member further has opposing ends defining shoulders for insert into a pair of overhang members on opposing ends of the arcuate groove. The arcuate board member has a centrally located boss plate with recess openings formed on opposing transverse sides. A switch body housing has a pair of convex ears rotatably mounted within the recess openings formed within the boss plate. The switch body includes a pair of opposing wall members frictionally insertable into the pair of fence walls formed on the lower surface of the visor. The switch body housing includes a switch for controlling on and off electrical connections from a battery mounted on a power board member insertable within the switch body. The battery is electrically coupled to the light on the board member whereby the hat structure may display the indicia by illumination of the light.

BRIEF DESCRIPTION OF THE DRAWINGS

FIG. 1A is an elevational view of the hat structure of the preferred embodiment showing differing indicia being displayed;

FIG. 1B is a perspective view of the visor portion of the hat structure;

DESCRIPTION OF THE PREFERRED EMBODIMENTS

Referring now to FIGS. 1-4, there is shown a hat structure for displaying indicia illuminated by a light mounted to the structure. In overall concept, the hat structure as herein described allows for indicia to be displayed by illumination of a light for advertising purposes or may even be used as an alarm system by the user. As shown in FIG. 1A, the hat structure may be used by the user to display differing indicia at the discretion of the person wearing the hat.

Figure 2:
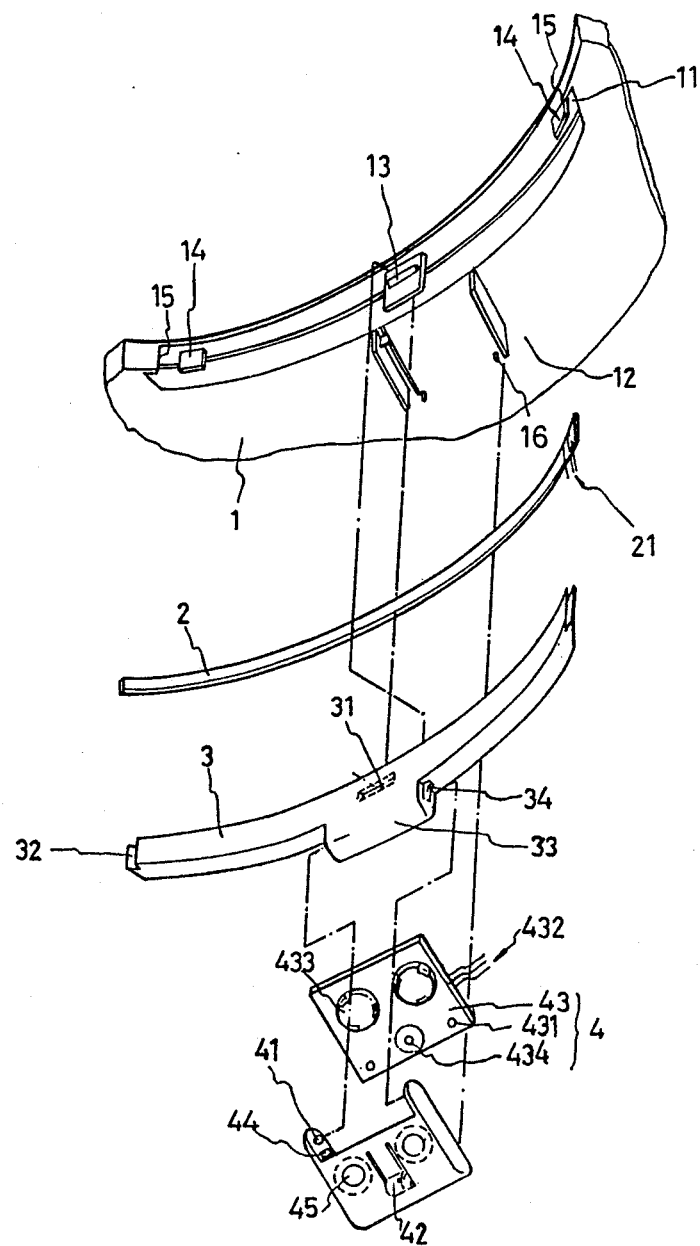
FIG. 2 is an exploded view of the subject hat structure.

Referring now to FIGS. 1B and 2, there is shown the hat structure which includes hat visor 1 which maybbe formed unitarily in molded construction. Visor 1 may be formed of a plastic composition or some like material. Visor 1 includes a lower surface having a pair of fence wall members 12 transversely displaced each from the other and extending frontally of said visor 1 from the lower surface thereof. Fence wall members 12 are generally planar and extend parallel each with respect to the other.

Visor 1 includes arcuate groove 11 formed therein in a rear section of visor 1 to the rear of fence wall members 12. Fence wall members 12 are spaced apart each from the other about a central location or position of arcuate groove 11. A pair of assist board members 14 extend from a wall defining arcuate groove 11. Assist board members are formed on substantially opposing ends of arcuate groove 11. Additionally, rib member 13 is formed within arcuate groove 11 and is generally formed at a central location of groove 11, as is clearly seen in FIG. 2.

Board member 2 having indicia formed thereon is illuminated by a light member (not shown) mounted on board member 2. Board member 2 may simply be a board member having predetermined indicia electrically coupled to a power supply, as will be seen in following paragraphs, or in the alternative, may even be a printed circuitboard which controls flashing of a light member mounted thereon to provide varying visual effects. The important consideration is that board member 2 may be mounted or inserted into the interior of arcuately directed groove 11 and contained therein.

Figure 3A:
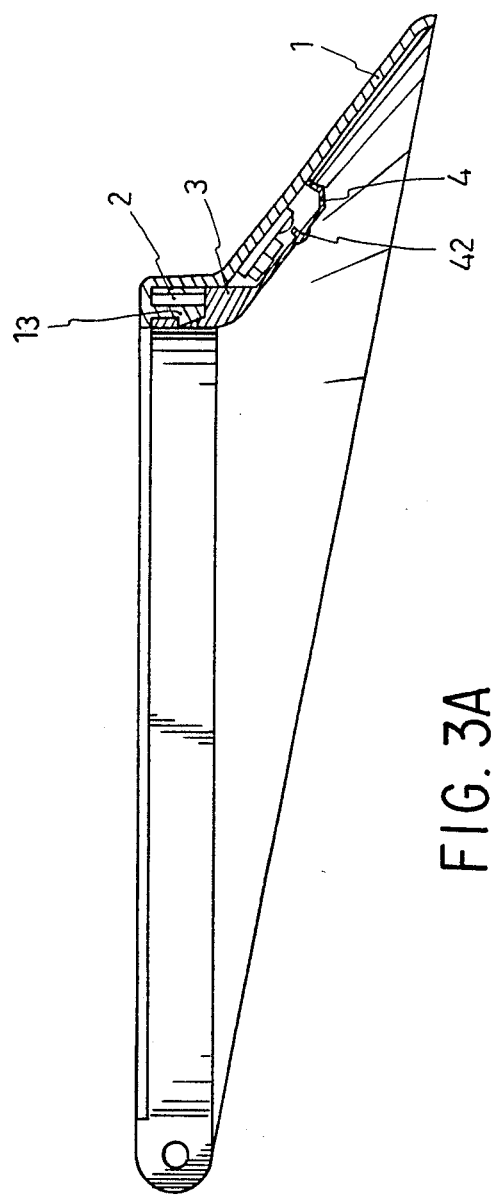
FIG. 3A is an elevational view partially cut-away showing the switch body housing in closed formation on the visor.
Figure 3B:
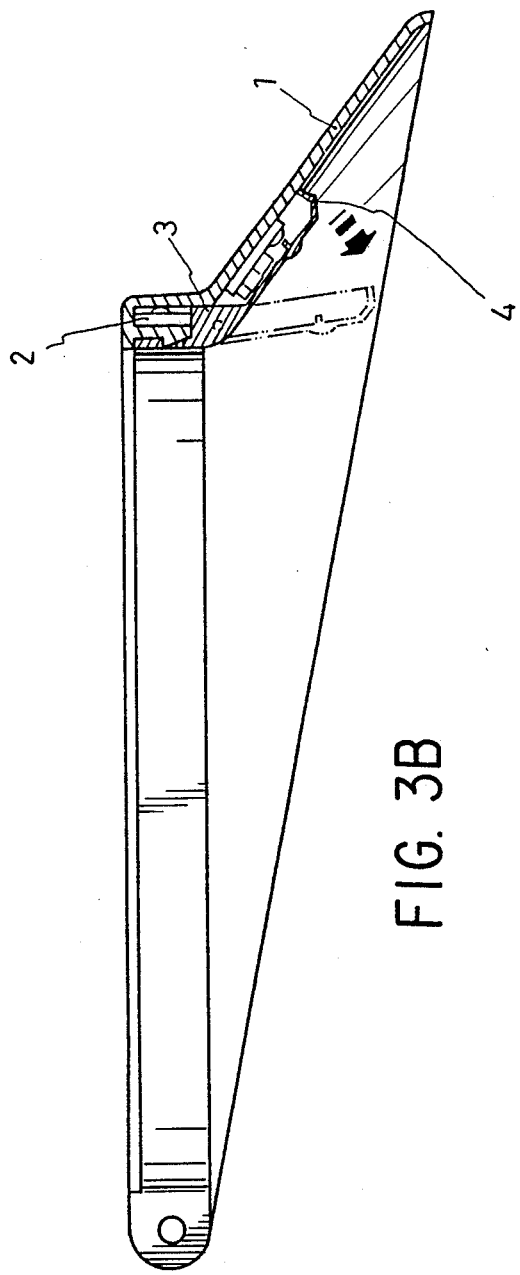
FIG. 3B is an elevation sectional drawing showing the opening of the switch body housing in phantom lines; and, FIG. 4 is a elevation sectional drawing showing the hat structure in operational contact.
Figure 4:
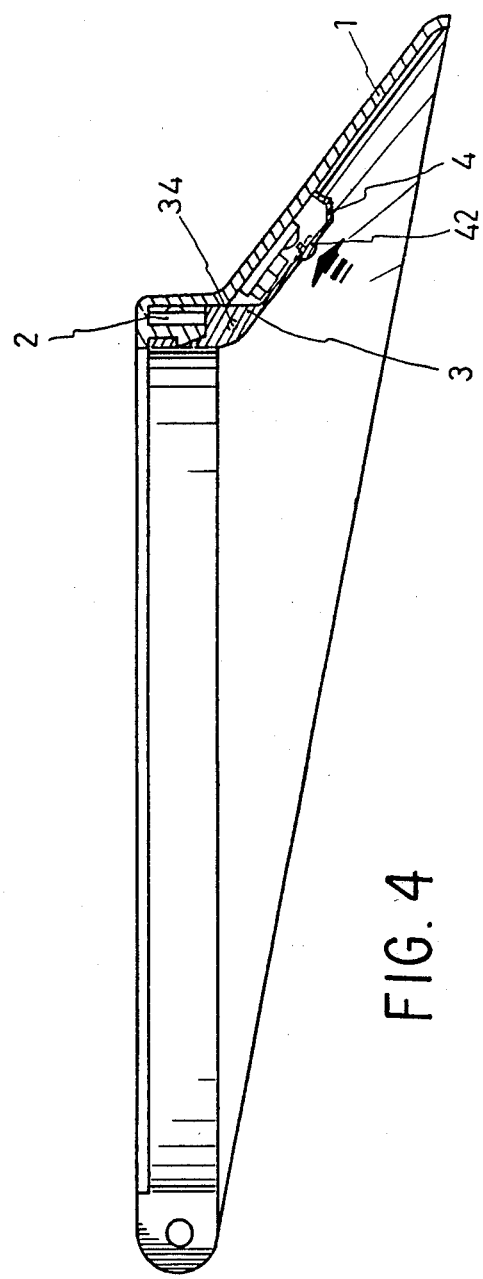

Subsequent to board member 2 being inserted in groove 11, arcuate board cover member may then be inserted to fit over board member 2 within groove 11 as is shown in FIGS. 3A, 3B, and 4. Arcuate board cover member 3 is fixedly mounted to visor 1 within groove 11 by insert of rib 13 within opening 31 formed within arcuate board cover member 3, as is shown in FIG. 2. Thus, arcuate board cover member 3 includes centrally located opening 31 for insert of rib member 13 therein for fixedly constraining both arcuate board cover member 3 and board member 2 within groove 11 of visor 1. Arcuate cover member 3 extends downwardly from the lower surface of visor 1 and as can be seen, is sandwiched between rib member 13 and fence wall members 12. In this manner, arcuate board cover member 3 and board member 2 may be easily inserted and assembled into operational contact within the overall hat structure.

As has previously been stated, boss plate 33 is located central to arcuate board cover member 3 and extends downwardly from a bottom portion thereof. Recess openings 34 on opposing transverse sides of boss plate 33 are provided to align with convex ear members 41 formed on a frontal portion of opposing walls of a housing of switch body 4. Switch body 4 includes a pair of opposing wall members which are frictionally insertable into fence wall members 12 formed on the lower surface of visor 1. By frictional insert of convex ear members 41 into recess openings 34, the housing of switch body 4 may be coupled to arcuate board cover member 3 in a rotationally displaceable manner. The housing of switch body 4 may rotate freely to an open or a closed position at the bottom of arcuate board cover member 3. Inner ribs 44 formed on opposing walls of the housing of switch body 4 may be used to interface with fence wall members 12 and provide for a frictionally held interface.

Power board 43 is fittingly engaged within the housing of switch body 4 and includes a battery 433 which is actuated by power switch 434. Power switch 434 is coupled in the normal fashion to elastic switch 42 on the housing of switch body 4 to close the circuit between battery 433 and wire leads 432 on power board 43 which are coupled to electrical leads 21 mounted on board member 2. In this manner, there is electrical coupling between power board 43 and printed circuitboard member 2 for actuation of control signals to an illumination light.

Batteries 433 on power board 43 extend into recess openings 45 formed within the housing of switch body 4 to provide a seating arrangement for batteries 433 and to maintain a constrained relation therebetween. Holes 431 formed through power board 43 are aligned with rib extensions 16 formed on the lower surface of visor 1 for insert thereof. In this manner, the overall structure of switch body 4 may be mounted in a reasonably constrained relation to the lower surface of visor 1. Additionally, the switch body 4 may be rotatably displaced with respect to the lower surface of visor 1 by insert of convex ear members 41 within recess openings 34 formed on boss plate 33.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is claimed is:

1. A hat structure for displaying indicia illuminated by a light mounted to said structure comprising:

a unitarily formed visor defining a lower surface having a pair of fence wall members extending therefrom, said visor having an arcuate groove formed therein, said visor having a pair of assist board members formed on opposing ends of said arcuate groove and a rib member formed substantially central of said arcuate groove;

a board member having said indicia formed therein and illuminated by said light mounted on said board member;

an arcuate board cover member for contiguously interfacing with said arcuate groove, said arcuate board cover member having a centrally located opening for insert of said rib member therein, said arcuate board cover member having opposing ends defining shoulders for insert into a pair of overhang members on opposing ends of said arcuate groove, said arcuate board cover member having a centrally located boss plate with recess openings formed on opposing transverse sides;

a switch body having a pair of convex ears rotatably mounted within said recess openings formed within said boss plate, said switch body including a pair of opposing wall members frictionally insertable into said pair of fence walls formed on said lower surface of said visor, said switch body including a switch for controlling on/off electrical connections from a battery mounted on a power board member insertable within said switch body, said battery being electrically coupled to said light on said board member whereby said hat structure may display said indicia by said light.

2. The hat structure as recited in claim 1 where said visor, arcuate board cover member and switch body are each molded in one-piece formation.

3. The hat structure as recited in claim 1 where said opposing wall members of said switch body include a pair of convexly formed ear members for releasable insert into said recess openings formed on opposing transverse sides of said boss plate, said switch body being rotationally displaceable with respect to said boss plate whereby said switch body may be opened and closed for access to said power board containing said battery.

* * * * *